United States Patent
Vasudevan et al.

(10) Patent No.: US 8,431,402 B2
(45) Date of Patent: Apr. 30, 2013

(54) **METHOD OF HIGH FREQUENCY REGENERATION OF *SORGHUM***

(75) Inventors: Ramesh Anbazhagan Vasudevan, Singapore (SG); Kumar Nadimuthu, Singapore (SG); Srinivasan Ramachandran, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 149 days.

(21) Appl. No.: 13/003,971

(22) PCT Filed: Jul. 23, 2008

(86) PCT No.: PCT/SG2008/000266
§ 371 (c)(1), (2), (4) Date: Jan. 13, 2011

(87) PCT Pub. No.: WO2010/011175
PCT Pub. Date: Jan. 28, 2010

(65) Prior Publication Data
US 2011/0124107 A1 May 26, 2011

(51) Int. Cl.
*C12N 5/00* (2006.01)
(52) U.S. Cl.
USPC .................. 435/430.1; 435/430; 800/320
(58) Field of Classification Search .................. 435/430, 435/430.1, 431; 800/320
See application file for complete search history.

(56) References Cited

U.S. PATENT DOCUMENTS 5,320,961 A * 6/1994 Zhong et al. .................. 435/424
2002/0164798 A1 * 11/2002 Eudes et al. .................. 435/424
2006/0070146 A1  3/2006 Pereira

FOREIGN PATENT DOCUMENTS

| EP | 0 176 162 A1 | 4/1986 |
|---|---|---|
| EP | 0176162 A1 * | 4/1986 |
| WO | 01/67861 A1 | 9/2001 |
| WO | 02/14520 A2 | 2/2002 |
| WO | 2005/029944 A2 | 4/2005 |

OTHER PUBLICATIONS

Baskaran et al. In vitro plant regeneration and mass propagation system for Sorghum bicolor—a valuable major cereal crop. Journal of Agricultural Technology 1(2) 345-363, 2005.*
Gaspar et al. Plant Hormones and Plant Growth Regulators in Plant Tissue Culture. In Vitro Cell. Dev. Biol.—Plant 32:272-289, 1996.*
Hagio. Adventitious shoot regeneration from immature embryos of sorghum. Plant Cell, Tissue and Organ Culture 68: 65-72, 2002.*
Howe et al. Rapid and reproducible Agrobacterium-mediated transformation of sorghum. Plant Cell Rep (2006) 25: 784-791.*
Jha et al. Somatic embryogenesis in Jatropha curcas Linn., an important biofuel plant. Plant Biotechnol Rep (2007) 1: 135-140.*
Purnhauser et al. Stimulation of shoot regeneration in Triticum aestivum and Nicotiana plumbaginifolia Viv. tissue cultures using the ethylene inhibitor AgNO3. Plant Cell Reports (1987) 6: 1-4.*
Qureshi et al. Modulation of somatic embryogenesis in early and late-stage embryos of wheat (*Triticum aestivum* L.) under the influence of abscisic acid and its analogs. Plant Cell, Tissue and Organ Culture 18: 55-69, 1989.*
Syamala, D et al., "Efficient regeneration of sorghum, *Sorghum bicolour* (L.) Moench, from shoot-tip explant," Indian Journal of Experimental Biology, (2003), vol. 41, No. 12, pp. 1482-1486.
Abscisic acid (retrieved on Oct. 6, 2008) Retrieved from internet http://en.wikipedia.org/wiki/Abscisic_acid, published on Nov. 18, 2007 as per Wayback Engine, 3 pp.

* cited by examiner

*Primary Examiner* — June Hwu
(74) *Attorney, Agent, or Firm* — Rothwell, Figg, Ernst & Manbeck, PC

(57) ABSTRACT

The present invention relates generally to the regeneration of *sorghum* involving organogenesis. More specifically, the present invention relates to a method of regenerating sorghum, particularly *Sorghum bicolor* (L.) Moench, via organogenesis that yields a high frequency of regenerants. In addition to providing high frequency regeneration, the present invention can be applied directly to the production of *sorghum* variants through somoclonal variation and to the genetic transformation of *sorghum*.

16 Claims, 1 Drawing Sheet

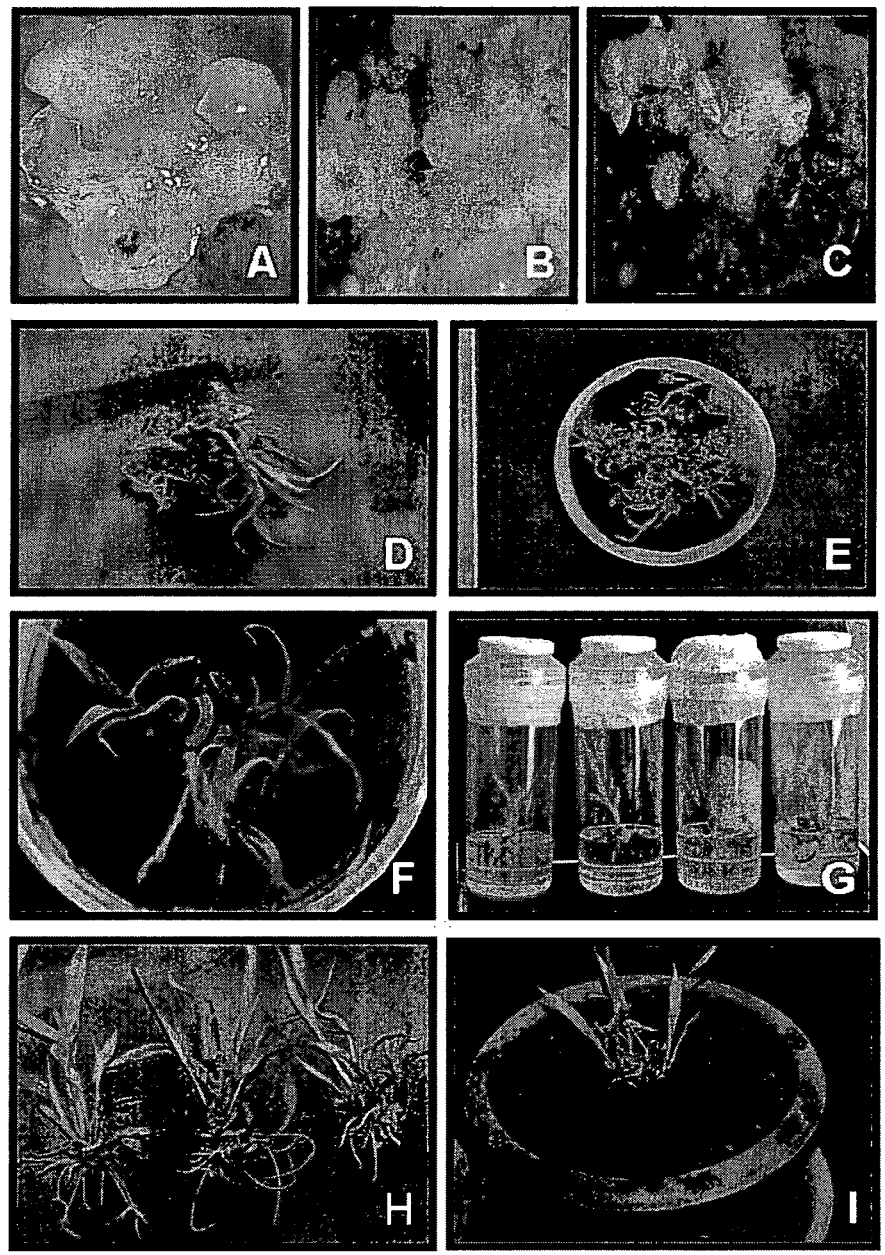

METHOD OF HIGH FREQUENCY REGENERATION OF SORGHUM

CROSS-REFERENCE TO RELATED APPLICATIONS

The present application is a national stage filing under 35 U.S.C. §371 of PCT/SG2008/000266, filed on 23 Jul. 2008, the disclosure of which is incorporated herein by reference.

BACKGROUND OF THE INVENTION

The present invention relates generally to the regeneration of sorghum involving organogenesis. More specifically, the present invention relates to a method of regenerating sorghum, particularly Sorghum bicolor (L.) Moench, via organogenesis that yields a high frequency of regenerants.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Sorghum (Sorghum bicolor (L.) Moench) is a widely grown grain and forage crop, and more closely related to the major crops of tropical origin such as rice, maize, sugarcane, and pearl millet. Sorghum ranks fifth in production among cereal crops, and is an important model for tropical grasses. It is unique among major cereals because it adapts well to environmental extremes, notably drought and heat. These attributes make sorghum the logical grain to support human and animal populations in areas with extreme heat and minimal precipitation (Howe et al. 2006). In addition, the current economic, environmental and energy security concerns worldwide forces to shift from fossil fuels to biofuel alternatives such as bioethanol and biodiesel. Since biofuels can be produced from a diverse set of crops, each country is adopting a strategy that exploits the comparative advantages it holds in certain crops.

Among the different biofuel crops, sorghum is considered to be a better candidate for the production of bioethanol because of the physiological and natural factors, including the fact that it is a photosynthetic efficient C4 plant. To further improve this crop, biotechnological techniques such as tissue culture and transformation can be utilized. Over three decades several reports were documented on sorghum regeneration using various explants using different composition of media. These reports include plant regeneration (immature embryos (Gamborg et al. 1977, Ma et al. 1987, Hagio 2002), shoot portions of mature embryos (Cai et al. 1987), Shoot apices (Zhong et al. 1988), mature embryos (Nirwan and Kothari, 2003), transverse thin layer cells of roots (Baskaran et al. 2006)), somatic embryogenesis (immature and mature embryos (Rao et al. 1995, Elkonin et al. 1996, MacKinnon et al. 1986), leaf base (Mishra and khurana, 2003)) and transformation (immature embryos (Zhao et al. 2000, Carvalho et al. 2004), immature and mature embryos, shoot tips and embryogenic callus (Tadesse et al. 2003) and shoot apices (Girijashankar et al. 2005), seeds (Howe et al. 2006)) in sorghum.

Despite these reported successes, it is desired to develop new techniques for the regeneration of sorghum. It is imperative that such techniques have high frequencies of regeneration which makes the techniques useful for the application of genetic manipulations such as biomass increase or sugar content increase to improve this crop for increased bioethanol production.

SUMMARY OF THE INVENTION

The present invention relates generally to the regeneration of sorghum involving organogenesis. More specifically, the present invention relates to a method of regenerating sorghum, particularly Sorghum bicolor (L.) Moench, via organogenesis that yields a high frequency of regenerants.

Thus, the present invention provides for the first time a method for the high frequency regeneration of sweet sorghum (Sorghum bicolor (L.) Moench). Briefly, sorghum is regenerated via organogenesis using dissected embryonated cotyledon (DEC) explants. The present invention is widely applicable to sweet sorghum varieties and hybrids, and is specifically illustrated herein with respect to sweet sorghum (Sorghum bicolor (L.) Moench) hybrid varieties Liotian 1, Lioza 7050A and Liao Ji Za 1. In addition to providing high frequency regeneration, the present invention can be applied directly to the production of sorghum variants through somoclonal variation and to the genetic transformation of sorghum.

In accordance with the present invention, organogenic callus is induced from dissected embryonated cotyledon (DEC) explants of Chinese sweet sorghum (Sorghum bicolor (L.) Moench) and plants are regenerated from the organogenic callus. The high frequency regeneration system of the present invention consists of six-stages: stage 1 (callus induction), stage 2 and 3 (shoot bud induction and reduction of phenolic exudates), stage 4 (shoot bud induction and elongation), stage 5 (shoot elongation and reduction of phenolic exudates) and stage 6 (rooting). MS mineral salts supplemented with N6 vitamins in stage 1, MS mineral salts supplemented with B5 vitamins in the subsequent stages and the alteration of antioxidants (e.g., polyvinyl pyrrolidone (PVP) and polyvinyl polypyrrolidone (PVPP)), organic additives (e.g., adenine sulfate ($AdSO_4$)), inorganic additives (e.g., $AgNO_3$), amino acids (e.g., L-proline, L-glutamine, L-glycine) and PGRs (plant growth regulators) at specific stages enhances the efficiency of regeneration and reduces the exudation of high phenolic compounds inherent in sorghum tissue culture. Approximately 250-300 healthy plantlets devoid of any significant variation in genotypes are produced from a single DEC explant within a short span of three months time with 100% survivability.

BRIEF DESCRIPTION OF THE FIGURE

FIGS. 1A-1I illustrate the regeneration of sorghum via organogenesis from dissected embryonated cotyledons (DEC) in accordance with the present invention. FIGS. 1A and 1B show dissected embryonated cotyledon explants without radicals and callus induction in and around the cotyledonary node. FIG. 1C shows shoot bud induction from the DEC callus. FIGS. 1D and 1E show multiple shoot regeneration from shoot buds. FIG. 1F shows elongation of the regenerated shoots. Figures G and H show rooting of the elongated shoots. FIG. 1I shows hardened plantlets.

DETAILED DESCRIPTION OF THE INVENTION

The present invention relates generally to the regeneration of sorghum involving organogenesis. More specifically, the present invention relates to a method of regenerating sorghum, particularly Sorghum bicolor (L.) Moench, via organogenesis that yields a high frequency of regenerants. In addition to providing high frequency regeneration, the present invention can be applied directly to the production of *sorghum* variants through somoclonal variation and to the genetic transformation of sorghum.

In the description which follows, the aspects of the invention may be described with reference to certain *sorghum* hybrids for convenience only. It is understood that other sorghum varieties and hybrids can be used in place of the referenced *sorghum* hybrids.

As used herein, "organogenesis" refers to the regeneration of shoots either via callus or direct meristematic tissues of any part of plants in a specific medium under controlled environmental conditions.

As used herein, "callus" refers to an unorganized or undifferentiated mass of proliferative cells produced from any explant tissue.

In accordance with the present invention, a method is provided for regenerating sorghum through organogenesis that efficiently yields a high frequency of regenerated plants. In one embodiment, plants are regenerated from explants obtained from embryonated cotyledon explants of sorghum, particularly *Sorghum bicolor* (L.) Moench. The embryonated cotyledon explants are dissected and placed on a solid medium, referred to as stage 1 medium herein. In one embodiment, the stage 1 medium comprises MS mineral salts and N6 vitamins and is supplemented with L-proline and L-glutamine. In one embodiment, the stage 1 medium is supplemented with about 25 mg to about 200 mg, preferably about 50 mg to about 100 mg, more preferably about 100 mg L-proline. In another embodiment, the stage 1 medium is supplemented with about 50 mg to about 250 mg, preferably about 50 mg to about 100 mg, more preferably about 100 mg L-glutamine. The stage 1 medium also contains plant growth regulators. In one embodiment, the plant growth regulators are an auxin and abscisic acid (ABA). In a preferred embodiment, the auxin is 2,4-dichlorophenoxy acetic acid (2,4-D). In one embodiment, the concentration of ABA in the stage 1 medium is about 0.94 µM to about 18.9 µM, preferably about 0.94 µM to about 7.56 µM, more preferably about 3.78 µM. In another embodiment, the concentration of 2,4-D in the stage 1 medium is about 2.26 µM to about 9.04 µM, preferably about 4.52 µM to about 6.78 µM, more preferably about 6.78 µM. The stage 1 medium also contains a source of carbon. In one embodiment, the source of carbon is sucrose at about 2% to about 5%, preferably about 2% to about 3%, more preferably, about 3%. In another embodiment, the source of carbon is glucose at about 2% to about 5%, preferably about 3% to about 5%. In an additional embodiment, the source of carbon is fructose at about 2% to about 5%, preferably about 2% to about 3%. In a further embodiment, the source of carbon is maltose at about 2% to about 5%, preferably about 2% to about 3%. In another embodiment, the source of carbon is a mixture of sucrose and glucose at about 2% to about 3%, preferably about 2% sucrose and about 2% to about 3%, preferably about 2% glucose. In an additional embodiment, the source of carbon is a mixture of fructose and glucose at about 1% to about 2%, preferably about 1% fructose and about 2% to about 3%, preferably about 2% glucose. In a further embodiment, the source of carbon is a mixture of maltose and glucose at about 1% to about 2%, preferably about 1% maltose and about 2% to about 3%, preferably about 2% glucose.

In one embodiment, the DEC segments are cultured on the stage 1 medium for about four weeks to about eight weeks, preferably about six weeks. In another embodiment, the stage 1 cultures are subcultured at about two week intervals. In one embodiment, the stage 1 culture is maintained at about 25° C.±2° C. with a 16 h/8 h (light/dark) photoperiod at 55% to 60% relative humidity. In one embodiment, the light photoperiod is under white fluorescent lights with a light intensity of about 25 $\mu m^{-2}s^{-1}$. The DEC segments free of radicals cultured on stage 1 medium show suppressed growth, but at the same time the explants became swollen, stumped and yellowish green. The plumules attached to the cotyledon bulged and became callused in and around the cotyledonary node (SCPC). The presence of ABA, proline and L-glutamine in the stage 1 medium induced stress and inhibited germination of embryos attached to the cotyledons. The presence of 2,4-D induced callus formation. Along with the plumules, the radical tissues also started to bulge within two weeks. These radical tissues were completely removed from the explants.

After culturing on the stage 1 medium, the SCPC is injured and placed on a solid medium referred to as stage 2 medium herein. In one embodiment, the stage 2 medium comprises MS mineral salts and B5 vitamins and is supplemented with L-proline, L-glutamine, L-glycine, ascorbic acid (Asc), AgNO$_3$, PVP and PVPP. In one embodiment, the stage 2 medium is supplemented with about 100 mg to about 1000 mg, preferably about 300 mg to about 600 mg, more preferably about 500 mg L-proline. In another embodiment, the stage 2 medium is supplemented with about 100 mg to about 1000 mg, preferably about 300 mg to about 600 mg, more preferably about 500 mg L-glutamine. In a further embodiment, the stage 2 medium is supplemented with Asc at a concentration of about 1.42 µM to about 11.36 µM, preferably about 2.84 µM to about 8.52 µM, more preferably about 5.67 µM. In one embodiment, the stage 2 medium is supplemented with about 0.25 g to about 1.5 g, preferably about 0.5 g to about 1.5 g, more preferably about 1.0 g PVP. In another embodiment, the stage 2 medium is supplemented with about 0.25 g to about 1.5 g, preferably about 0.5 g to about 1.0 g, more preferably about 1.0 g PVPP. In a further embodiment, the stage 2 medium is supplemented with about 2 mg to about 20 mg, preferably about 5 mg to about 15 mg, more preferably about 10 mg L-glycine. In another embodiment, the stage 2 medium is supplemented with about 0.2 mg to about 1.5 mg, preferably about 0.5 mg to about 1.0 mg, more preferably about 1.0 mg AgNO$_3$. The stage 2 medium also contains a plant growth regulator. In one embodiment, the plant growth regulator is an auxin. In a preferred embodiment, the auxin is (2,4-D. In one embodiment, the concentration of 2,4-D in the stage 2 medium is about 2.26 µM to about 9.04 µM, preferably about 4.52 µM to about 6.78 µM, more preferably about 6.78 µM. The stage 2 medium also contains a source of carbon. The source of carbon in the stage 2 medium may be the same as in the stage 1 medium. In a preferred embodiment, the source of carbon is sucrose at about 2% to about 5%, preferably about 2% to about 3%, more preferably, about 3%.

In one embodiment, the injured SCPC is cultured on the stage 2 medium for about three days to about seven days, preferably about five days. In another embodiment, the stage 2 culture is maintained at about 25° C.±2° C. with a 16 h/8 h (light/dark) photoperiod at 55% to 60% relative humidity as described above. During this period, shoot buds started to induce from the plumular callus as well as in and around the cotyledonary node. Simultaneously, enormous phenolic exudates started oozing out from the base of the shoot buds. The addition of Asc, PVP, PVPP, L-glycine and AgNO$_3$ to the stage 2 medium prevented these phenolic exudates. Long time culture of SCPC more than five days in stage 2 medium inhibited the developing shoot buds which simultaneously, became brown and ultimately senesced.

After culturing on the stage 2 medium, the tissue is placed on a solid medium referred to as stage 3 medium herein. In one embodiment, the stage 3 medium comprises MS mineral salts and B5 vitamins and is supplemented with L-glutamine, L-glycine, casein hydrolysate (CH), adenine sulfate ($AdSO_4$) and PVP. In one embodiment, the stage 3 medium is supplemented with about 100 mg to about 1000 mg, preferably about 300 mg to about 600 mg, more preferably about 500 mg L-glutamine. In a another embodiment, the stage 3 medium is supplemented with about 5 mg to about 25 mg, preferably about 10 mg to about 20 mg, more preferably about 20 mg L-glycine. In a further embodiment, the stage 3 medium is supplemented with about 0.25 g to about 1.5 g, preferably about 0.5 g to about 1.5 g, more preferably about 1.0 g PVP. In one embodiment, the stage 3 medium is supplemented with about 0.5 g to about 1.5 g, preferably about 0.5 g to about 1.0 g, more preferably about 1.0 g CH. In another embodiment, the stage 3 medium is supplemented with about 25 mg to about 200 mg, preferably about 50 mg to about 100 mg, more preferably about 100 mg $AdSO_4$. The stage 3 medium also contains plant growth regulators. In one embodiment, the plant growth regulators are auxins and cytokinins. In a preferred embodiment, the auxin is 2,4-D. In one embodiment, the concentration of 2,4-D in the stage 3 medium is about 0.56 µM to about 2.24 µM, preferably about 0.56 µM to about 1.12 µM, more preferably about 1.12 µM. In a preferred embodiment, the cytokinins are a mixture of 6-benzylaminopurine (BA) and kinetin (KN). In one embodiment, the concentration of BA in the stage 3 medium is about 4.43 µM to about 13.29 µM, preferably about 4.43 µM to about 11.07 µM, more preferably about 8.86 µM. In another embodiment, the concentration of KN in the stage 3 medium is about 2.32 µM to about 18.56 µM, preferably about 4.64 µM to about 13.92 µM, more preferably about 9.28 µM. The stage 3 medium also contains a source of carbon. The source of carbon in the stage 3 medium may be the same as in the stage 1 medium. In a preferred embodiment, the source of carbon is sucrose at about 2% to about 5%, preferably about 2% to about 3%, more preferably, about 3%.

In one embodiment, the tissue is cultured on the stage 3 medium for about seven days to about 15 days, preferably about ten days. In another embodiment, the stage 3 cultures are subcultured at about five day intervals. In one embodiment, the stage 3 culture is maintained at about 25° C.±2° C. with a 16 h/8 h (light/dark) photoperiod at 55% to 60% relative humidity as described above. In the stage 3 medium, auxin (2,4-D) concentration was reduced, cytokinins, (BA, KN) and organic additives (such as CH, $AdSO_4$, PVP) were added to enhance shoot bud proliferation and growth.

After culturing on the stage 3 medium, the proliferating shoot buds from a single clump are split into 8-10 clumps with each clump containing three to five shoot buds and cultured on a solid medium referred to as stage 4 medium herein. In one embodiment, the stage 4 medium comprises MS mineral salts and B5 vitamins and is supplemented with L-glycine and adenine sulfate ($AdSO_4$). In one embodiment, the stage 4 medium is supplemented with about 5 mg to about 25 mg, preferably about 10 mg to about 20 mg, more preferably about 20 mg L-glycine. In another embodiment, the stage 4 medium is supplemented with about 25 mg to about 200 mg, preferably about 50 mg to about 100 mg, more preferably about 100 mg $AdSO_4$. The stage 4 medium also contains plant growth regulators. In one embodiment, the plant growth regulators are a cytokinin and gibberellic acid ($GA_3$). In a preferred embodiment, the cytokinin is BA. In one embodiment, the concentration of BA in the stage 4 medium is about 4.43 µM to about 13.29 µM, preferably about 4.43 µM to about 11.07 µM, more preferably about 8.86 µM. In another embodiment, the concentration of $GA_3$ in the stage 4 medium is about 0.72 µM to about 2.88 µM, preferably about 0.72 µM to about 2.16 µM, more preferably about 1.44 µM. The stage 4 medium also contains a source of carbon. The source of carbon in the stage 4 medium may be the same as in the stage 1 medium. In a preferred embodiment, the source of carbon is sucrose at about 2% to about 5%, preferably about 2% to about 3%, more preferably, about 3%.

In one embodiment, the proliferating shoot buds are cultured on the stage 4 medium for about one week to about three weeks, preferably about two weeks. In another embodiment, the stage 4 cultures are subcultured at about one week intervals. In one embodiment, the stage 4 culture is maintained at about 25° C.±2° C. with a 16 h/8 h (light/dark) photoperiod at 55% to 60% relative humidity as described above. After two weeks about 25-30 shoot buds with shoot regeneration occurred from each single clump. Plant growth regulators (PRGs) (2,4-D and KN) and organic additives (PVP,CH, L-glutamine) were removed and $GA_3$ were supplemented for shoot elongation in stage 4. Injuries occur to the tissue when the shoot buds are split from the clumps, and these injuries result in phenolic secretion such that the base of the tissue becomes brownish black.

After culturing on the stage 4 medium, the proliferating shoot buds are cultured on a solid medium referred to as stage 5 medium herein. In one embodiment, the stage 5 medium comprises MS mineral salts and B5 vitamins and is supplemented with L-glycine, PVP and adenine sulfate ($AdSO_4$). In one embodiment, the stage 5 medium is supplemented with about 5 mg to about 25 mg, preferably about 10 mg to about 20 mg, more preferably about 20 mg L-glycine. In another embodiment, the stage 5 medium is supplemented with about 25 mg to about 200 mg, preferably about 50 mg to about 100 mg, more preferably about 100 mg $AdSO_4$. in a further embodiment, the stage 5 medium is supplemented with about 0.25 g to about 1.5 g, preferably about 0.5 g to about 1.0 g, more preferably 1.0 g PVP. The stage 5 medium also contains plant growth regulators. In one embodiment, the plant growth regulators are a cytokinin and gibberellic acid ($GA_3$). In a preferred embodiment, the cytokinin is BA. In one embodiment, the concentration of BA in the stage 5 medium is about 4.43 µM to about 13.29 µM, preferably about 4.43 µM to about 11.07 µM, more preferably about 8.86 µM. In another embodiment, the concentration of $GA_3$ in the stage 5 medium is about 0.72 µM to about 2.88 µM, preferably about 0.72 µM to about 2.16 µM, more preferably about 1.44 µM. The stage 5 medium also contains a source of carbon. The source of carbon in the stage 5 medium may be the same as in the stage 1 medium. In a preferred embodiment, the source of carbon is sucrose at about 2% to about 5%, preferably about 2% to about 3%, more preferably, about 3%.

In one embodiment, the proliferating shoot buds are cultured on the stage 5 medium for about one week to about three weeks, preferably about two weeks. In another embodiment, the stage 5 cultures are subcultured at about one week intervals. In one embodiment, the stage 5 culture is maintained at about 25° C.±2° C. with a 16 h/8 h (light/dark) photoperiod at 55% to 60% relative humidity as described above. To avoid further browning of the tissue, PVP is added to the stage 5 medium as an anti-oxidizing agent. The PVP does not inhibit the shoot growth but enhances shoot proliferation. The shoot proliferation and growth was maximum (4 cm) in stage 5 medium within two weeks.

After culturing on the stage 5 medium, the shoot clumps with 2-3 shoots of approximately 4 cm in height are transferred to a solid medium referred to as stage 6 medium herein for rooting. In one embodiment, the stage 6 medium comprises MS mineral salts and B5 vitamins and is supplemented with L-glycine, PVP and adenine sulfate (AdSO$_4$). In one embodiment, the stage 6 medium is supplemented with about 5 mg to about 25 mg, preferably about 10 mg to about 20 mg, more preferably about 20 mg L-glycine. In another embodiment, the stage 6 medium is supplemented with about 25 mg to about 200 mg, preferably about 50 mg to about 100 mg, more preferably about 100 mg AdSO$_4$. In a further embodiment, the stage 6 medium is supplemented with about 0.25 g to about 1.5 g, preferably about 0.5 g to about 1.0 g, more preferably 1.0 g PVP. The stage 6 medium also contains a plant growth regulator. In one embodiment, the plant growth regulator is an auxin. In a preferred embodiment, the auxin is indole 3-acetic acid (IAA). In one embodiment, the concentration of IAA in the stage 6 medium is about 2.85 µM to about 11.4 µM, preferably about 2.85 µM to about 8.55 µM, more preferably about 5.7 µM. The source of carbon in the stage 6 medium may be the same as in the stage 1 medium. In a preferred embodiment, the source of carbon is sucrose at about 2% to about 5%, preferably about 2% to about 3%, more preferably, about 3%.

In one embodiment, the proliferating shoot buds are cultured on the stage 6 medium for about one week to about three weeks, preferably about two weeks. In one embodiment, the stage 6 culture is maintained at about 25° C.±2° C. with a 16 h/8 h (light/dark) photoperiod at 55% to 60% relative humidity as described above. The auxin, IAA in stage 6 medium, induced roots within one week. There was no root formation on plant growth regulator free medium or medium containing only cytokinins. Auxin was essential for root induction and without auxin, there was no root formation. An average of 10-15 roots of 3 cm long are produced per shoot when cultured in stage 6 medium. The rooted plantlets are successfully hardened with about 100% survivability and transferred to the green house for further growth.

In addition, the present invention provides systems which can be used for the in transformation of *sorghum* plants so that high frequency of transgenic plants can be obtained. The method of transformation/transfection is not critical to the transformation of sorghum plants; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed. See, for example, Mathews et al. (1992), Neuhaus et al. (1987), Wilde et al. (1992), U.S. Pat. Nos. 7,241,937, 7,273,966 and 7,291,765 and U.S. Patent Application Publication Nos. 2007/0231905 and 2008/0010704 (U.S. Pat. No. 7,906,705 B2). See also, International Published Application No. WO2005/103271.

In one embodiment, the explant tissue can be co-cultured with an *Agrobacterium* strain harboring one or more DNA constructs containing one or more genes or nucleic acids of interest using techniques well known in the art. Transformed tissue can be selected using conventional techniques well known in the art. In a further embodiment, the DNA can be introduced into the explant tissue using conventional techniques, such as particle bombardment. Transformed tissue can be selected using conventional techniques well known in the art. Transformed or transgenic plants can be regenerated using the methods described herein.

Similarly, the DNA that is inserted (the DNA of interest) into *sorghum* plants is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616 (U.S. Pat. No. 8,058,512 B2). The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 (U.S. Pat. No. 8,058,512 B2) and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters is described in U.S. Pat. Nos. 6,506,962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616 (U.S. Pat. No. 8,058,512 B2).

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al. 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Selection of Plant Materials

Seeds of sweet *sorghum* (*Sorghum bicolor* (L.) Moench) hybrid varieties Liotian 1, Lioza 7050A and Liao Ji Za 1 were obtained from Chinese National Center for *Sorghum* Improvement, Shenyang City, 110161, Liaoning Province, P.R. China. The viable seeds were washed in chlorohexidine surgical wash (two drops in 100 ml of sterile water) for five minutes and soaked in sterile water for two days at 4° C. in refrigerator. Later these imbibed seeds were further surface sterilized in 10% clorox solution (commercial bleach) for 10 minutes followed by washes with sterile water for five times. To ensure complete sterility, these seeds were rinsed again with 70% alcohol for 90 seconds and subsequently washed with sterile water three times before used as explants.

Example 2

Regeneration System and Culture Conditions

The seed coats were removed from the sterilized seeds of all the three hybrid varieties (Liotian 1, Lioza 7050A and Liao Ji Za 1) and the embryonated cotyledon explants were dissected and inoculated aseptically on the stage 1 medium (Table 1) for swelling, callusing of plumules in and around the cotyledonary nodal regions (SCPC). The radical tissues were completely removed from the dissected embryonated cotyledon (DEC) explants. After six weeks of culture, the SCPC from stage 1 medium were further injured and transferred to stage 2 medium (Table 1) and stage 3 medium (Table 1) at five and ten-day interval for shoot bud induction. Subsequently, the shoot buds developed on stage 3 medium were split into 8-10 clumps with each clumps containing three to five shoots and transferred to stage 4 medium (Table 1) for further shoot induction followed by stage 5 medium (Table 1) for shoot elongation at two-week intervals respectively. The elongated shoot clumps with 2-3 shoots (4 cm height) from stage 5 medium were transferred to stage 6 medium (Table 1) for root induction. The well developed and rooted plantlets were transferred for hardening after two weeks of culture.

TABLE 1

Media Compositions and Culture Periods

| Media | Composition of Media | Effect | Culture Period |
|---|---|---|---|
| Stage 1 | MS salts + N6 vitamins + 2,4-D (6.78 µM) + L-Proline (100 mg) + L-Glutamine (100 mg) + ABA (3.78 µM) + Sucrose (3%) | Swelling, callusing of plumules in and around the cotyledonary nodal regions (SCPC) | Six-weeks |
| Stage 2 | MS salts + B5 vitamins + L-Proline (500 mg) + L-Glutamine (500 mg) + 2,4-D (6.78 µM) + Asc (5.67 µM) + PVP(1.0 g) + PVPP (0.5 g) + L-Glycine (10 mg) + $AgNO_3$ (1.0 mg) + Sucrose (3%) | Shoot bud induction and reduction of phenolic exudates | Five-days |
| Stage 3 | MS salts + B5 vitamins + L-Glutamine (500 mg) + 2,4-D (1.12 µM) + BA (8.86 µM) + KN (9.28 µM) + PVP (1 g) + CH (1.0 g) + L-Glycine (20 mg) + $AdSO_4$ (100 mg) + Sucrose (3%) | Shoot bud induction and reduction of phenolic exudates | Ten-days |
| Stage 4 | MS salts + B5 vitamins + L-Glycine (20 mg) + BA (8.86 µM) + GA3 (1.44 µM) + $AdSO_4$ (100 mg) + Sucrose (3%) | Shoot bud induction and elongation | Two-weeks |
| Stage 5 | MS salts + B5 vitamins + L-Glycine (20 mg) + PVP (1.0 g) + $AdSO_4$ (100 mg) + BA (8.86 µM) + $GA_3$ (1.44 µM) + Sucrose (3%) | Shoot elongation and reduction of phenolic exudates | Two-weeks |
| Stage 6 | MS salts + B5 vitamins + L-Glycine (20 mg) + PVP (1.0 g) + $AdSO_4$ (100 mg) + IAA (5.7 µM) + Sucrose (3%) | Rooting of elongated shoots | Two-weeks |
| | Total period taken to establish regeneration from dissected embryonated cotyledons | | ~Twelve-weeks |

MS: Murashige and Skoog's mineral salts.
N6 vitamin: Nitch and Nitch vitamins.
2,4-D: 2,4-dichlorophenoxy acetic acid.
ABA: abscisic acid.
B5 vitamin: Gamborg vitamins.
Asc: ascorbic acid.
PVP: polyvinylpyrrolidone.
PVPP: polyvinylpolypyrrolidone.
BA or BAP: 6-benzylamniopurine or benzyl adenine.
KN: kinetin.
CH: casein hydrolysate.
$AdSO_4$: adenine sulfate.
$GA_3$: gibberellic acid.
IAA: indole 3-acetic acid.

The pH of the medium was adjusted to 5.8 with 1N NaOH or 1N HCl prior to the addition of 0.8% phytoagar (stages 1-5 media) or 0.25% phytogel (stage 6 medium) and sterilized by autoclaving at 121° C. for 20 minutes. Approximately 20 ml of sterilized medium was dispensed into sterilized Petri dish (90×15 mm size, plastic polycarbonate, Canada). The chemicals used for media preparations were of analytical grade (Duchefa Biochemie, Haarlem, The Netherlands and Sigma Aldrich, Inc., St Louis, USA). All the cultures were maintained at 25° C. 2° C. under white fluorescent tube lights, 16/8 h (light/dark) photoperiod period, light intensity of 25 µE $m^{-2}s^{-1}$ and with 55-60% relative humidity. The cultures were subcultured at two-week intervals during stage 1, five-day intervals in stages 2 and 3, followed by one-week intervals in stages 4 and 5, with no subculturing in stage 6.

Example 3

High Frequency Regeneration of Sorghum

The DEC segments free of radicals (FIGS. 1A and B) cultured on stage 1 medium showed suppressed growth, but at the same time the explants became swollen, stumped and yellowish green. The plumules attached to the cotyledon bulged and became callused in and around the cotyledonary node (SCPC). Similar results were reported in immature cotyledon explants of Vigna unguiculata (Prem Anand et al. 2001). The proliferation of callus occurred in a slow phase with low amount (FW 0.5 g). The presence of ABA, proline and L-glutamine in the stage 1 medium induced stress and inhibited germination of embryos attached to the cotyledons. The presence of 2,4-D induced callus formation.

Along with the plumules, the radical tissues also started to bulge within two weeks. These radical tissues were completely removed from the explants. Sub-culturing was carried out at two week intervals. After six weeks of culture in stage 1 medium, the SCPC (FW 0.5 g) were injured and transferred to stage 2 medium for a short duration of 5 days with subsequent transfer to stage 3 medium for ten days. During this period, shoot buds started to induce from the plumular callus as well as in and around the cotyledonary node (FIG. 1C). Simultaneously, enormous phenolic exudates started oozing out from the base of the shoot buds. In order to avoid these phenolic exudates, Asc, PVP, PVPP, glycine and $AgNO_3$ were added to stage 2 medium. Based on our observations, long time culture of SCPC more than five days in stage 2 medium inhibited the developing shoot buds which simultaneously, became brown and ultimately senesced. This could be due to PVPP and AgNO$_3$ acting as inhibitors of the tissue growth when cultured for a long time. To avoid this browning and senescing, subculture was done at five days interval. Our observations coincide with those of Zhao et al. (2000) who have reported the negative impacts of associated phenolic compound production from *sorghum* tissue culture and can be overcome by short subculture intervals and the addition of PVPP to tissue culture media. In contrast, Carvalho et al. (2004) reported that the addition of PVP or PVPP to the inoculation, co-cultivation or post-co-cultivation media slightly reduced browning of immature embryos and did not improve embryo survival during *Agrobacterium* transformation. Similarly, Rao et al. (1995) observed that, all sweet *sorghum* genotypes produced anthocyanins leading to purple, brown or reddish black calli formation and can be removed by the addition of activated charcoal and decreasing the subculturing time.

In stage 3 medium, auxin (2,4-D) concentration was reduced, cytokinins, BA, KN and organic additives such as CH, AdSO$_4$, PVP were added to enhance shoot bud proliferation and growth. After ten-days, the proliferating shoot buds from a single clump were split into 8-10 clumps with each clump containing three to five shoot buds and cultured on stage 4 medium. After two weeks it was observed that, around 25-30 shoot buds with shoot regeneration occurred from each single clump (FIGS. 1D and E). Thus, we obtained a high frequency of regeneration of around 200 to 300 shoots from a single explant. Plant growth regulators (PRGs) (2,4-D and KN) and organic additives (PVP, CH, L-glutamine) were removed and GA$_3$ were supplemented for shoot elongation.

Once the shoot buds were split from the clumps, phenolic secretion occurred due to injuries, and the tissues at the base became brownish black in stage 4 medium. To avoid this browning, PVP was further supplemented in stage 5 medium. PVP acted as an antioxidizing agent and did not inhibit the shoot growth but enhanced shoot proliferation. The shoot proliferation and growth was maximum (4 cm) in stage 5 medium within two weeks (FIG. 1F). The shoot clumps with 2-3 shoots of approximately 4 cm in height were transferred to stage 6 medium for rooting. The auxin, IAA in stage 6 medium, induced roots within one week (FIGS. 1G and 1H). It was observed that there was no root formation on plant growth regulator free medium or medium containing only cytokinins. Auxin was essential for root induction and without auxin, there was no root formation. An average of 10-15 roots of 3 cm long were produced per shoot when cultured in stage 6 medium. The rooted plantlets were successfully hardened with the (100%) survivability and transferred to the green house (FIG. 1I).

Cai et al. (1987) have developed organogenic system from shoot portions of mature embryo in three stages, stage 1 modified MS medium with higher concentration of 2,4-D and lower concentration of KN and in stage 2, MS medium with lower concentration of 2,4-D and higher concentration of KN for callus induction followed by stage 3, MS medium with lower concentration of KN with or without α-naphthalene acetic acid (NAA) for regeneration of plantlets. They also stated that, amino acid L-asparagine was essential for the regeneration system and the efficiency of plant regeneration is around 11-8% and over all, 700 plants were obtained after a prolonged period of nine months. On the other hand, Baskaran et al. (2006) have reported maximum percentage of callus induction from root explants of *sorghum* on MS medium supplemented with 2,4-D and coconut water (CW), shoot bud induction and elongation (BAP, 2,4-D and CW) and root induction on half strength MS medium with IAA. They have also stated that the frequency of regeneration is around 90% with 65 shoots per callus explants and took sixteen weeks to get complete plantlets.

Based on the literature regarding *sorghum* regeneration system as described above, our regeneration system using DEC explants of *sorghum* differs and we put forth that, MS salts with N6 vitamins in stage 1, MS salts with B5 vitamins in subsequent stages and the alteration of antioxidants (PVP and PVPP), organic additives (AdSO$_4$), inorganic additives (AgNO$_3$), amino acids (L-proline, L-glutamine and L-glycine) and PGRs at specific stages is pivotal to enhance the efficiency of regeneration and reduce the high phenolic compounds associated in sorghum tissue culture. We would also like to highlight that, from a single dissected embryonated cotyledon explants (DEC), approximately 250-300 healthy plantlets can be produced with in a short span of three months time without any significant variation in genotypes. These results are in contradiction to the reports of Mackinnon et al. (1986), Cai et al. (1987), Rao et al. (1995) and Hagio et al. (2002), who stated that the efficiency of regeneration system in *sorghum* is genotype dependent. The present regeneration system can be directly applied for production of mutants through somaclonal variation, genetic transformation of desired genes such as involved in bioethanol and biomass increase.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Baskaran, P. and Jayabalan. N. (2006). Development of an In vitro regeneration system in sorghum (*Sorghum bicolor* (L.) Moench) using root transverse thin cell layers (tTCLs). *Turk J Bot* 30:1-9.

Cai, T. et al. (1987). Callus induction and plant regeneration from shoot portions of mature embryos of high tannin sorghums. *Plant Cell Tiss Org Cult* 9:245-252.

Carlos Henrique, S. et al. (2004). *Agrobacterium*-mediated transformation of sorghum: factors that affect transformation efficiency. *Gene Mol Biol* 27:259-269.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

Elkonin, L. A., et al. (1996). Embryogenic callus of *sorghum* (*Sorghum bicolor* (L.) Moench) by aminoacids. *Maydica* 40:153-157.

Gamborg, O. L. et al. (1977). Morphogenesis and plant regeneration from callus of immature embryos of sorghum. *Plant Sci Lett* 10:67-74.

Girijashankar, V. et al. (2005). Development of transgenic *sorghum* for insect resistance against the spotted stem borer (*Chilo partellus*). *Plant Cell Rep* 24:513-522

Hagio, T. (2002). Adventitious shoot regeneration from immature embryos of sorghum. *Plant Cell Tiss Org Cult* 68:65-72.

Howe, A. et al. (2006). Rapid and reproducible *Agrobacterium*-mediated transformation of sorghum. *Plant Cell Rep* 25:784-791.

Last, D. I. et al. (1991). pEmu: an improved promoter for gene expression in cereal cells. *Theor Appl Genet* 81:581-588.

Ma, H. et al. (1987). Plant regeneration from cultured immature embryos of *Sorghum bicolor* (L.) Moench. *Theor App Genet* 73:389-394.

Mackinnon, C. et al. (1986). Plant regeneration by somatic embryogenesis from callus cultures of sweet sorghum. *Plant Cell Rep* 5:349-351.

Mathews, H. et al. (1992). Stable integration and expression of beta-glucuronidase and NPT-II genes in mango somatic embryos. *In Vitro Cell Develop Biol—Plant* 28P:172-178.

McElroy, D. et al. (1990). Isolation of an efficient actin promoter for use in rice transformation. *Plant Cell* 2:163-171.

Mishra, A. and Khurana, P. (2003). Genotype dependent somatic embryogenesis and regeneration from leaf base cultures of *Sorghum bicolor*. *J Plant Biochem Biotech* 12:53-56.

Murashige, T. and Skoog, F. (1962). A revised medium for rapid growth and bioassays with tobacco tissue cultures. *Physiol Plant* 15:473-497.

Neuhaus, G. et al. (1987). Transgenic rapeseed plants obtained by microinjected DNA into microspore-derived embryoids. *Theor Appl Genet* 75:30-36.

Nirwan, R. S. and Kothari, S. L. (2003). High copper levels improve callus induction and plant regeneration in *Sorghum bicolor* (L.) Moench. *In Vitro Cell Dev Biol Plant* 39:161-164.

Nitsch, J. P. and Nitsch, C. (1969). Haploid plants from pollen grains. *Science* 169:85-87.

Odell, J. T. et al. (1985). Identification of DNA sequences required for activity of the cauliflower mosaic virus 35S promoter. *Nature* 313:810-812.

Prem Anand. R. et al. (2001). Plant regeneration from immature cotyledon-derived callus of *Vigna unguiculata* (L.) Walp (cowpea). *Current Sci* 80:671-674.

Rao, A. M. et al. (1995). Enhanced plant regeneration in grain and sweet *sorghum* by asparagines, proline and cefotaxime. *Plant Cell Rep* 15:72-75.

Tadesse, Y. et al. (2003). Optimisation of transformation conditions and production of transgenic *sorghum* (Sorghum bicolor) via microparticle bombardment. *Plant Cell Tiss Org Cult* 75:1-18.

Velten, J. et al. (1984). Isolation of a dual plant promoter fragment from the Ti plasmid of *Agrobacterium tumefaciens*. *EMBO J* 3:2723-2730.

Wilde, H. D. et al. (1992). Expression of foreign genes in transgenic yellow-poplar plants. *Physiol* 98:114-120.

Zhao, Z. Y. et al. (2000). *Agrobacterium*-mediated *sorghum* transformation. *Plant Mol Biol* 44: 789-798.

Zhong, H. et al. (1988). In vitro regeneration of *Sorghum bicolor* (L.) Moench: efficient plant regeneration from shoot apices. *J Plant Physiol* 153:719-726.

What is claimed is:

1. A method of regenerating sorghum via organogenesis comprising the steps:
   (a) culturing a sorghum explant on a first medium comprising MS mineral salts, N6 vitamins, 25 mg to 200 mg L-proline, 50 mg to 250 mg L-glutamine, a carbon source, 2.62 µM to 9.04 µM 2,4-dichlorophenoxy acetic acid (2,4-D) and 0.94 µM to 18.9 µM abscisic acid (ABA) to produce swelling and callusing of plumules in and around cotyledon nodal regions (SCPC), wherein the sorghum explant is a dissected embryonated cotyledon;
   (b) injuring the SCPC and culturing the injured SCPC on a second medium comprising MS mineral salts, B5 vitamins, 100 mg to 1000 mg L-proline, 100 mg to 1000 mg L-glutamine, 2 mg to 20 mg L-glycine, 1.42 µM to 11.36 µM ascorbic acid, 0.25 g to 1.5 g polyvinyl pyrrolidone (PVP), 0.25 g to 1.5 g polyvinyl polypyrrolidone (PVPP), 0.2 mg to 1.5 mg $AgNO_3$, a carbon source and 2.26 µM to 9.04 µM 2,4-D to induce shoot buds;
   (c) culturing tissue with induced shoot buds on a third medium comprising MS mineral salts, B5 vitamins, 100 mg to 1000 mg L-glutamine, 5 mg to 25 mg L-glycine, 0.25 g to 1.5 g PVP, 25 mg to 200 mg adenine sulfate ($AdSO_4$), 0.5 g to 1.5 g casein hydrolysate (CH), a carbon source, 0.56 µM to 2.26 µM 2,4-D, 4.43 µM to 13.29 µM 6-benzylaminopurine (BA) and 2.32 µM to 18.56 µM kinetin to enhance shoot bud proliferation and growth;
   (d) splitting the tissue with proliferating shoot buds into clumps of tissue with proliferating shoot buds;
   (e) culturing tissue with proliferating shoot buds on a fourth medium comprising MS mineral salts, B5 vitamins, 5 mg to 25 mg L-glycine, 25 mg to 200 mg $AdSO_4$, a carbon source, 4.43 µM to 13.29 µM BA and 0.72 µM to 2.88 µM gibberellic acid ($GA_3$) to enhance shoot growth;
   (f) culturing tissue with growing shoots on a fifth medium comprising MS mineral salts, B5 vitamins, 5 mg of 25 mg L-glycine, 0.25 g to 1.5 g PVP, 25 mg to 200 mg $AdSO_4$, a carbon source, 4.43 µM to 13.29 µM BA and 0.72 µM to 2.88 µM $GA_3$ to further enhance shoot growth; and
   (g) culturing tissue with growing shoots on a sixth medium comprising MS mineral salts, B5 vitamins, 5 mg to 25 mg L-glycine, 0.25 g to 1.5 g PVP, 25 mg to 200 mg $AdSO_4$, a carbon source and 2.85 µM to 11.4 µM indole 3-acetic acid (IAA) to induce root formation.

2. The method of claim 1, wherein the length of culturing on each medium is:
   about six weeks on the first medium;
   about five days on the second medium;
   about ten days on the third medium;

about two weeks on the fourth medium;
about two weeks on the fifth medium; and
about two weeks on the sixth medium.

3. The method of claim 1, wherein:
the culturing on the first medium is performed with subculturing about every two weeks;
the culturing on the third medium is performed with subculturing after about every 5 days;
the culturing on the fourth medium is performed with suculturing after about every week; and
the culturing on the fifth medium is performed with subculturing after about every week.

4. The method of claim 3, wherein the length of culturing on each medium is:
about six weeks on the first medium;
about five days on the second medium;
about ten days on the third medium;
about two weeks on the fourth medium;
about two weeks on the fifth medium; and
about two weeks on the sixth medium.

5. The method of claim 1, wherein the media comprise:
(a) first medium: MS mineral salts, N6 vitamins, about 50 mg to about 100 mg L-proline, about 50 mg to about 100 mg L-glutamine, about 4.52 µM to about 6.78 µM 2,4-D and about 0.94 µM to about 7.56 µM ABA;
(b) second medium: MS mineral salts, B5 vitamins, about 300 mg to about 600 mg L-proline, about 300 mg to about 600 mg L-glutamine, about 5 mg to about 15 mg L-glycine, about 2.84 µM to about 8.52 µM ascorbic acid, about 0.5 g to about 1.5 g PVP, about 0.5 g to about 1.0 g PVPP, about 0.5 mg to about 1.0 mg $AgNO_3$ and about 4.52 µM to about 6.78 µM 2,4-D;
(c) third medium: MS mineral salts, B5 vitamins, about 300 mg to about 600 mg L-glutamine, about 10 mg to about 20 mg L-glycine, about 0.5 g to about 1.5 g PVP, about 50 mg to about 100 mg $AdSO_4$, about 0.5 g to about 1.0 g CH, about 0.56 µM to about 1.12 µM 2,4-D, about 4.43 µM to about 11.07 µM BA and 4.64 µM to about 13.92 µM KN;
(d) fourth medium: MS mineral salts, B5 vitamins, about 10 mg to about 20 mg L-glycine, about 50 mg to about 100 mg $AdSO_4$, about 4.43 µM to about 11.07 µM BA and about 0.72 µM to about 2.16 µM $GA_3$;
(e) fifth medium: MS mineral salts, B5 vitamins, about 10 mg to about 20 mg L-glycine, about 0.5 g to about 1.0 g PVP, about 50 mg to about 100 mg $AdSO_4$, about 4.43 µM to about 11.07 µM BA and about 0.72 µM to about 2.16 µM $GA_3$; and
(f) sixth medium: MS mineral salts, B5 vitamins, about 10 mg to about 20 mg L-glycine, about 0.5 g to about 1.0 g PVP, about 50 mg to about 100 mg $AdSO_4$ and about 2.85 µM to about 8.55 µM IAA.

6. The method of claim 1, wherein the media comprise:
(a) first medium: MS mineral salts, N6 vitamins, about 100 mg L-proline, about 100 mg L-glutamine, about 6.78 µM 2,4-D and about 3.78 µM ABA;
(b) second medium: MS mineral salts, B5 vitamins, about 500 mg L-proline, about 500 mg L-glutamine, about 5 mg to about 15 mg L-glycine, about 5.67 µM ascorbic acid, about 1.0 g PVP, about 1.0 g PVPP, about 1.0 mg $AgNO_3$ and about 6.78 µM 2,4-D;
(c) third medium: MS mineral salts, B5 vitamins, about 500 mg L-glutamine, about 20 mg L-glycine, about 1.0 g PVP, about 100 mg $AdSO_4$, about 1.0 g CH, about 1.12 µM 2,4-D, about 8.86 µM BA and 9.28 µM KN;
(d) fourth medium: MS mineral salts, B5 vitamins, about 20 mg L-glycine, about 100 mg $AdSO_4$, about 8.86 µM BA and about 0.72 µM to about 1.44 µM $GA_3$;
(e) fifth medium: MS mineral salts, B5 vitamins, about 20 mg L-glycine, about 1.0 g PVP, about 100 mg $AdSO_4$, about 8.86 µM BA and about 1.44 µM $GA_3$; and
(f) sixth medium: MS mineral salts, B5 vitamins, about 20 mg L-glycine, about 1.0 g PVP, about 100 mg $AdSO_4$ and about 5.7 µM IAA.

7. The method of claim 1, wherein the source of carbon is selected from the group consisting of sucrose, glucose, fructose, maltose, a mixture of sucrose and glucose, a mixture of fructose and glucose and a mixture of maltose and glucose.

8. The method of claim 7, wherein the source of carbon is selected from the group consisting of about 2% to about 5% sucrose; about 2% to about 5% glucose; about 2% to about 5% fructose; about 2% to about 5% maltose; a mixture of about 2% to about 3% sucrose and about 2% to about 3% glucose; a mixture of 1% to about 2% fructose and about 2% to about 3% glucose; and a mixture of 1% to about 2% maltose and about 2% to about 3% glucose.

9. The method of claim 5, wherein the source of carbon is selected from the group consisting of sucrose, glucose, fructose, maltose, a mixture of sucrose and glucose, a mixture of fructose and glucose and a mixture of maltose and glucose.

10. The method of claim 9, wherein the source of carbon is selected from the group consisting of about 2% to about 5% sucrose; about 2% to about 5% glucose; about 2% to about 5% fructose; about 2% to about 5% maltose; a mixture of about 2% to about 3% sucrose and about 2% to about 3% glucose; a mixture of 1% to about 2% fructose and about 2% to about 3% glucose; and a mixture of 1% to about 2% maltose and about 2% to about 3% glucose.

11. The method of claim 6, wherein the source of carbon is selected from the group consisting of sucrose, glucose, fructose, maltose, a mixture of sucrose and glucose, a mixture of fructose and glucose and a mixture of maltose and glucose.

12. The method of claim 11, wherein the source of carbon is selected from the group consisting of about 2% to about 5% sucrose; about 2% to about 5% glucose; about 2% to about 5% fructose; about 2% to about 5% maltose; a mixture of about 2% to about 3% sucrose and about 2% to about 3% glucose; a mixture of 1% to about 2% fructose and about 2% to about 3% glucose; and a mixture of 1% to about 2% maltose and about 2% to about 3% glucose.

13. The method of claim 8, wherein the source of carbon is about 2% to about 3% sucrose.

14. The method of claim 10, wherein the source of carbon is about 2% to about 3% sucrose.

15. The method of claim 12, wherein the source of carbon is about 2% to about 3% sucrose.

16. The method of claim 1, wherein the culturing on each medium is performed at 25° C.±2° C., 55% to 60% relative humidity and a 16 h/8 h (light/dark) photoperiod.

* * * * *